US00PP30175P3

(12) United States Plant Patent
Stephens

(10) Patent No.: US PP30,175 P3
(45) Date of Patent: Feb. 5, 2019

(54) RASPBERRY PLANT NAMED 'NN12026'

(50) Latin Name: ***Rubus idaeus* L.**
Varietal Denomination: NN12026

(71) Applicant: Pacific Berries LLC, Lynden, WA (US)

(72) Inventor: Joseph Stephens, Auckland (NZ)

(73) Assignee: Pacific Berries LLC, Lynden, WA (US)

( * ) Notice: Subject to any disclaimer, the term of this patent is extended or adjusted under 35 U.S.C. 154(b) by 0 days.

(21) Appl. No.: 15/731,928

(22) Filed: Aug. 24, 2017

(65) Prior Publication Data

US 2018/0064008 P1 Mar. 1, 2018

Related U.S. Application Data

(60) Provisional application No. 62/379,928, filed on Aug. 26, 2016.

(51) Int. Cl.
*A01H 5/08* (2018.01)
*A01H 6/74* (2018.01)

(52) U.S. Cl.
USPC ..... Plt./204
CPC ..... *A01H 5/08* (2013.01); *A01H 6/7499* (2018.05)

(58) Field of Classification Search
USPC ..... Plt./156, 203, 204
See application file for complete search history.

*Primary Examiner* — Susan McCormick Ewoldt
*Assistant Examiner* — Karen M Redden
(74) *Attorney, Agent, or Firm* — Leydig, Voit & Mayer, Ltd.

(57) ABSTRACT

A new and distinct variety of *Rubus idaeus* L. named 'NN12026' and characterized by a dwarf plant habit, spineless canes, and red, moderately large fruit.

4 Drawing Sheets

Genus and species plant claimed: *Rubus idaeus* L.
Variety denomination: 'NN12026'.

BACKGROUND OF THE INVENTION

The new variety of red raspberry, *Rubus idaeus* L., was created in the course of a planned breeding program carried out at Lynden, Wash., USA. It was selected from a population of seedlings derived from a controlled cross carried out in 2009 between NR19 (seed parent) (not patented) and ZN06017 (pollen parent) (not patented). The original plant of the new variety was selected in 2012, based on its dwarf character, spineless cane and fruit quality. In 2014, 'NN12026' was asexually propagated in Lynden, Wash., USA, by root division and the original seedling plant was divided to form a two plant observation plot. Further propagation was carried out by tissue culture and replicated trials were established in 2016. The plant is not suited to commercial fruit production but is well suited to ornamental uses such as in the home garden and containers.

SUMMARY OF THE INVENTION

'NN12026' is characterised by its dwarf plant habit typically growing to a height of less than 80 cm, spineless canes and red, moderately large fruit.

The variety was first asexually propagated in 2014 by root division and subsequently propagated by tissue culture. The resulting plants propagated true to type from both root division and tissue culture, demonstrating that the characteristics of the new cultivar are stable and are transmitted without change through succeeding generations.

'NN12026' is distinguished from the dwarf raspberry 'NR7' (U.S. Plant Pat. No. 22,141) as 'NN12026' fruit shape is conical while 'NR7' is ovate. Cane pubescence is absent on 'NN12026' canes while 'NR7' has cane pubescence.

When compared to the pollen parent ZN06017 the new variety was found to have much shorter cane length.

When compared to the seed parent NR19 the new variety was found to have much shorter cane length, and in addition 'NN12026' is spineless while NR19 has spines.

BRIEF DESCRIPTION OF THE DRAWINGS

The accompanying photographs show typical specimens of the plant, foliage and fruit of the new variety as depicted in colors as nearly true as is reasonably possible to make the same in a color illustration of this character. The photographs were taken on mature plants in Washington State, USA.

DETAILED DESCRIPTION

Horticultural terminology is used in accordance with UPOV guidelines for raspberry. All dimensions in millimeters, weights in grams (unless otherwise stated). Where a color reference is given these refer to The R.H.S. Colour Chart, The Royal Horticultural Society, London, 4$^{th}$ edition, 2001. The specimens described were grown in Lynden, Washington State, USA.

Environmental data for the Lynden (48.95° N, 122.44° W), Wash., USA growing area demonstrates conditions in spring and early summer (equating to the harvest period for the variety) as follows:

Spring (April/May); mean daily temperature in the range 10-11° C. (mean daily minimum 5.5° C., mean daily maximum 15.5° C.).

Early summer (June/July); mean daily temperature 16° C. (mean daily minimum 10° C., mean daily maximum 21.5° C.).

In winter temperatures below 0° C. are common, the daily mean for December/January is 2.5° C. with the lowest temperature unlikely to be colder than −13° C. Average annual rainfall is approximately 1500 mm.

Figure 1:
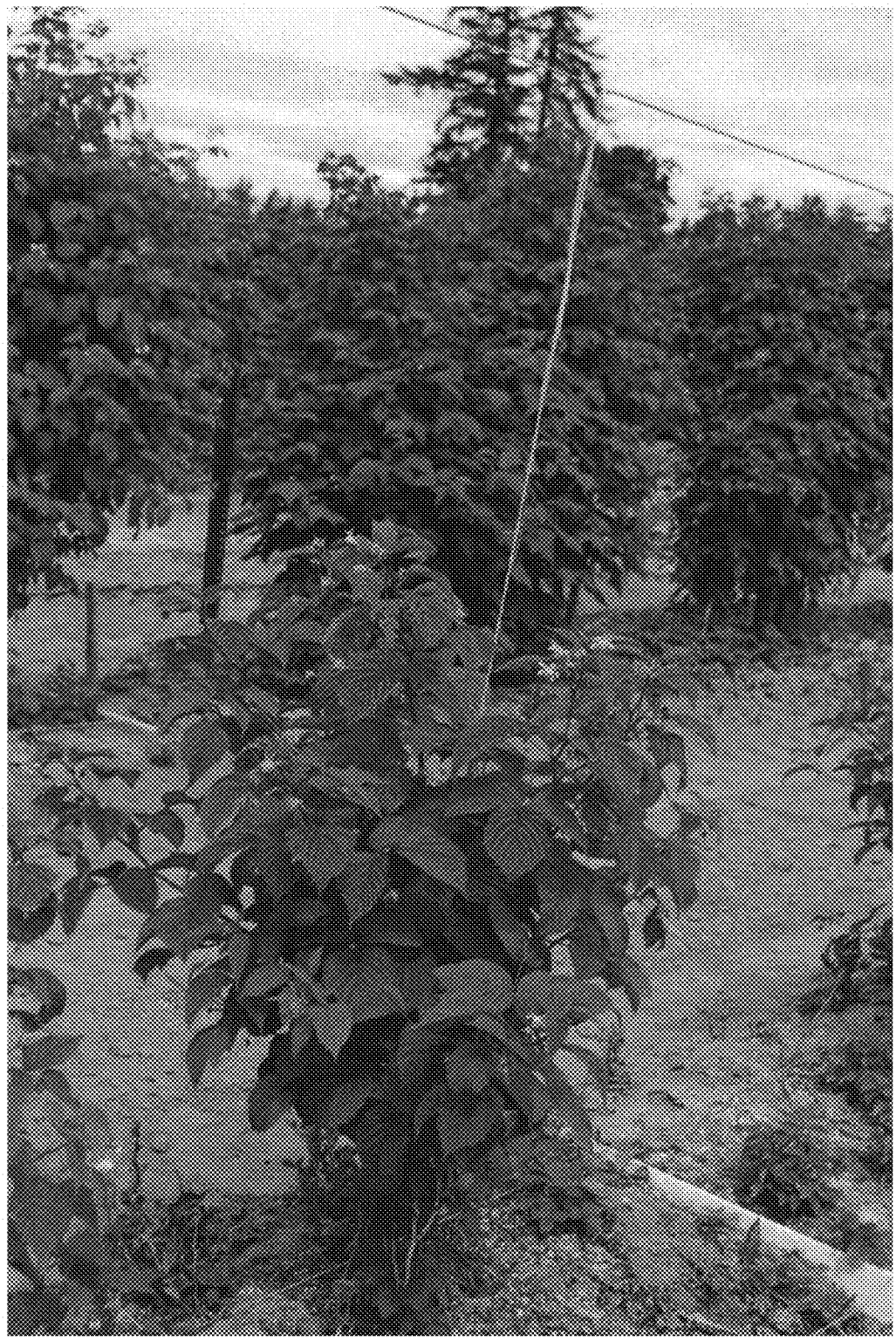
FIG. 1: One year old 'NN12026' field grown plant.
Figure 2:
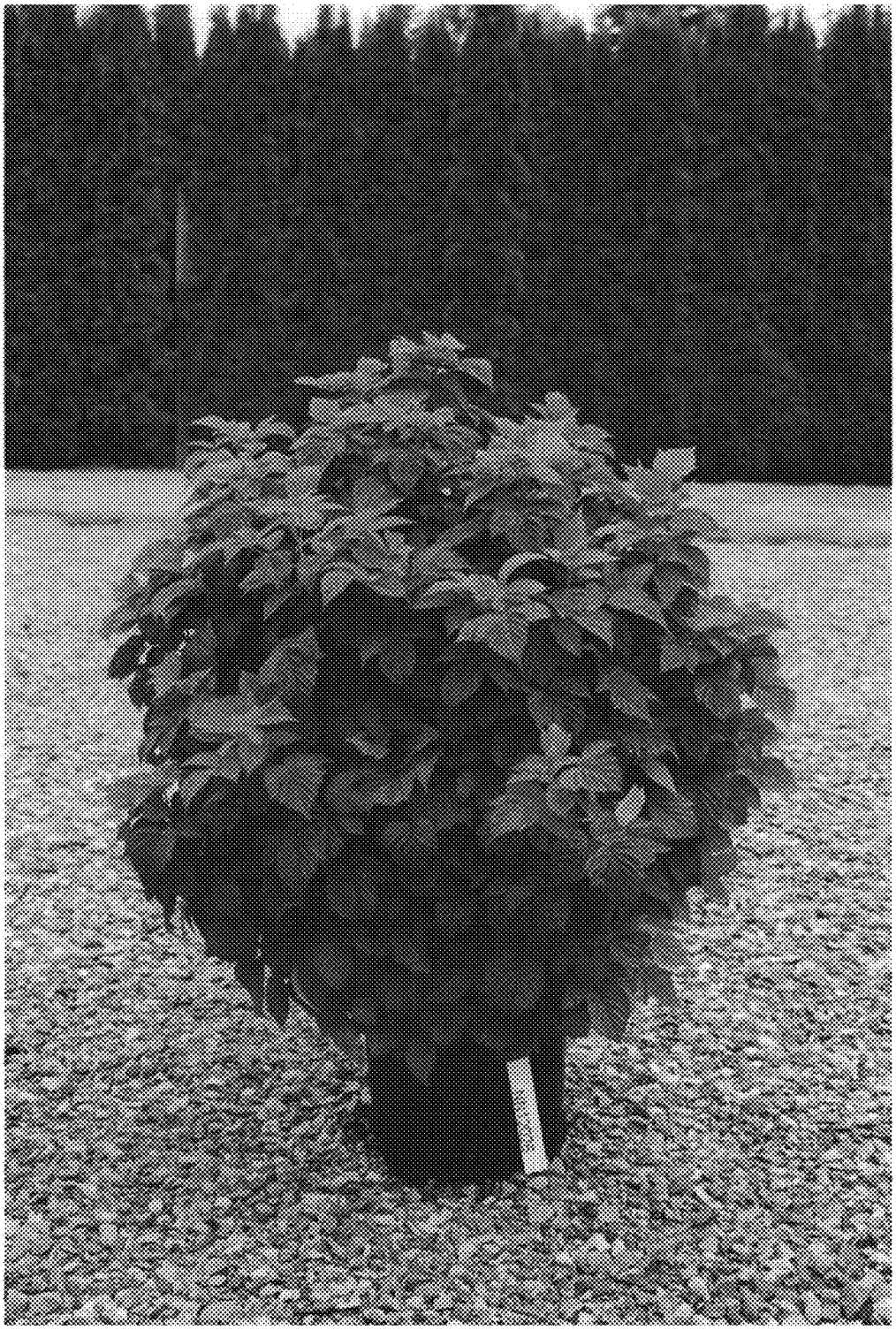
FIG. 2: Two year old 'NN12026' container grown plant
Figure 3:
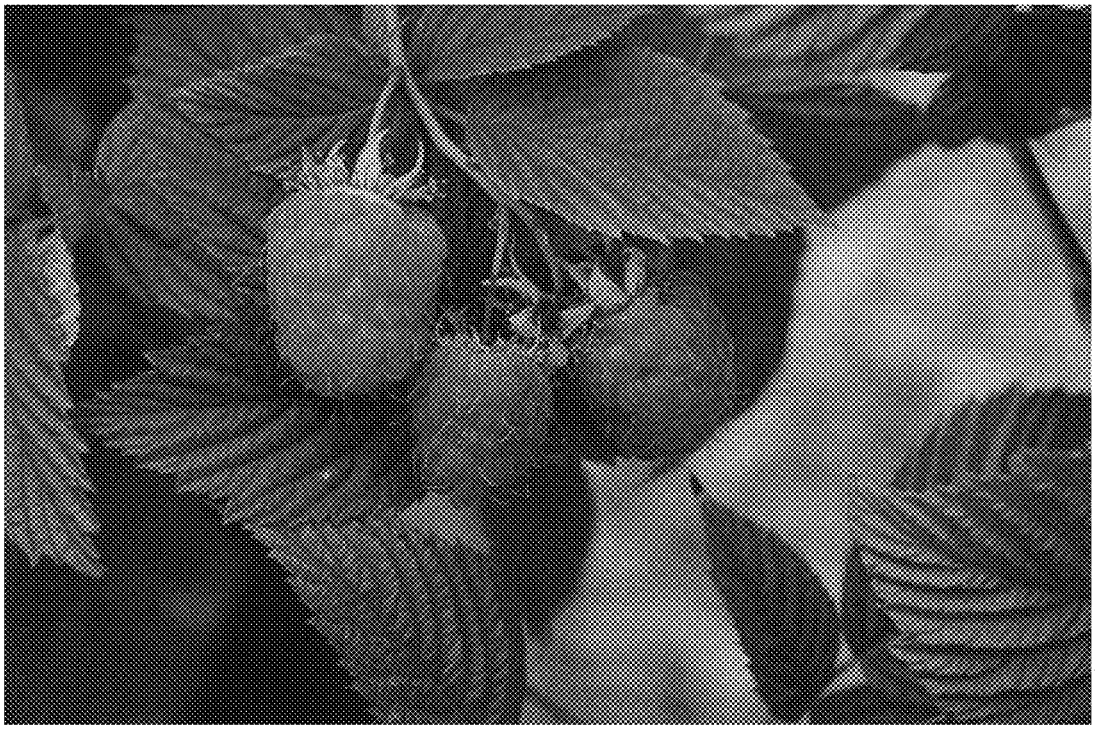
FIG. 3: 'NN12026' fruit on two year old plant
Figure 4:
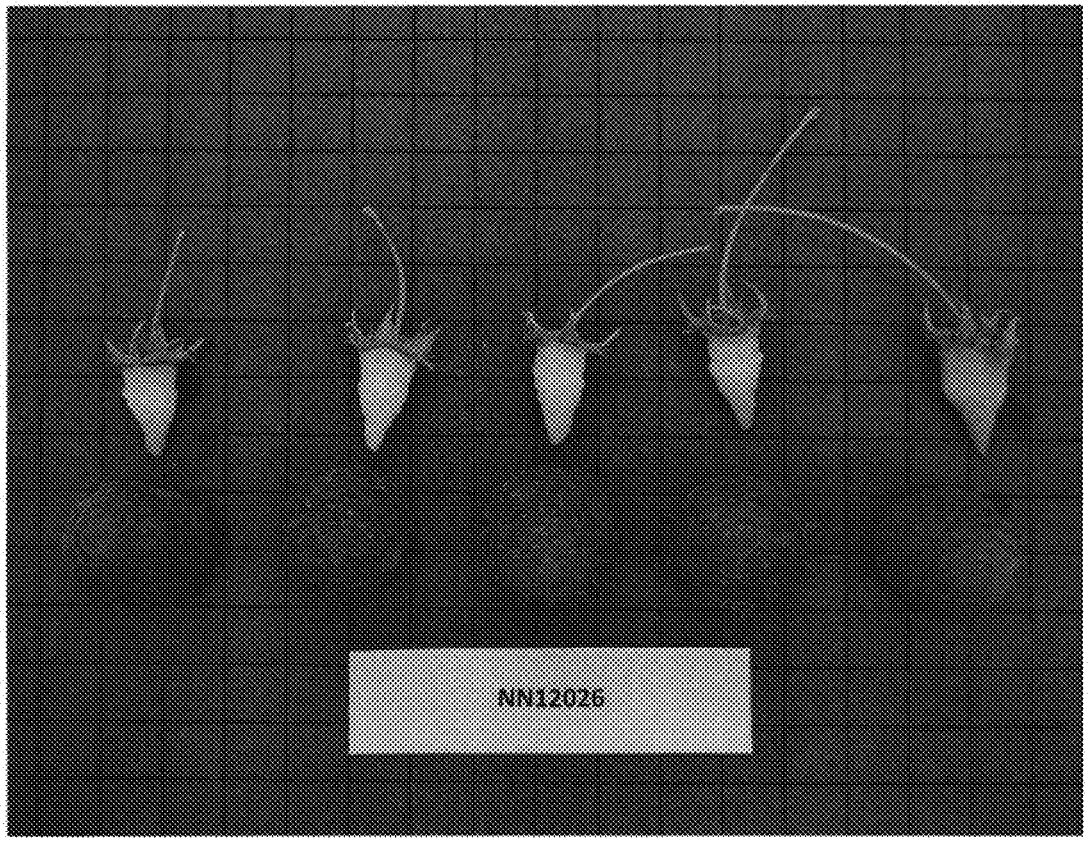
FIG. 4: 'NN12026' fruit and receptacle

Plant and foliage: plants exhibit a very strong dwarf growth habit (FIGS. 1 and 2). Mature plant height is commonly less than 80 cm and canes length is short typically ranging from 50-70 cm. Internode length is in the range 25-40 mm and nodes/cane average 23. Spines are absent. Canes have pubescence indicating the presence of the gene H. The hairs are sparse and fine. During the growing season generally the coloration on the cane is yellow-green, near 145B and no anthocyanin coloration is evident on the sun-exposed side of the cane. Young shoots are upright in attitude and similar in color to the mature cane.

The leaves are compound, moderately puckered and concave in shape in cross section. The number of primocane leaflets per internode is ranged from 3-5. The terminal leaflet is frequently fused with one or both lateral leaflets. The base of the terminal leaflet is cordate in shape and typically the shape of the apex is pointed. The average terminal leaflet length is 65 mm and average width 49 mm. The leaflets are free to slightly overlapping. The coloration of the upper surface of the leaf is green to yellow-green, ranging from near 137B to 146A. The underside being markedly lighter in coloration (near Greyed-green 194A). The margin of the leaf is biserrate. The leaf petiole typically averages 36 mm in length and 3 mm in diameter. It is near Yellow-green 145A in color and anthocyanin coloration is present on the upper side of the petiole near 185A. The fruit is borne on the previous year's growth.

Inflorescence: white flowers are borne on short slender pedicel which are approximately 23 mm in length and 0.9 mm in diameter. Flowers are borne on a paniculate inflorescence. Typically there are five petals, obovate in shape with an obtuse apex and truncate base. The petals average approximately 6.5-8.0 mm in length and 3.0-4.5 mm in width. They are typically smooth in texture, have an entire margin and are near White 155C in color. The pedicel length averages approximately 23 mm long and approximately 0.9 mm in diameter and is near Yellow-green 144B in color and has weak anthocyanin coloration on the sun-exposed side (near Red-purple 60A). A typical king flower average diameter is approximately 24 mm (from sepal tip to sepal tip i.e. the widest part of the flower). The flowers are predominantly borne singly although pairs are present. The flowers have no discernible fragrance. Five sepals are present and are Yellow-green in color, near 147D and on average measure approximately 9 mm in length from base to tip. The reproductive organs are typical for flowers of *Rubus idaeus* L.; the stigmas average approximately 75 in number and are near Yellow-green 145C in color; there are approximately 80 stamens the filaments of which are near White 155C in color and average 5 mm in length. Anthers are brown and (depending on maturity) near Yellow-white 158B in color.

Harvest: fruit commences ripening typically in late June in Washington U.S.A. The main harvest period is complete by late July. Due to its dwarfing habit the plant produces an associated lower yield of fruit compared with taller growing varieties.

Fruit: Fruit is produced on previous year's cane in summer. The average berry weight is approximately 4.2 g; individual fruit ranging between 3-5 g in weight. Fruit shape is conical. On average berries are 21.3 mm long and 20.8 mm wide at the widest point. Fruit color is medium red; external and internal color is near 187B. Fruit drupelet size has been observed to be medium (typically average diameter is 4.6 mm) and drupelet number typically averages 66 per fruit. The berries have moderate firmness. The seeds average 2.7 mm long and 1.6 mm wide, and are near 159B in color when dry. Seed numbers per fruit average 61 and weigh on average 0.135 g per fruit (or average 2.2 mg individually).

Pest and disease resistance: Raspberry Bushy Dwarf Virus (RBDV) has not been detected in this variety using enzyme-linked immunosorbent assay (ELISA) tests and RBDV has never been detected in trial plots of 'NN12026'.

Geographical adaptation: observations indicate that the variety is well-suited to production in regions that offer a medium amount of winter chill, for example, 'NN12026' performs in USDA Plant Hardiness zones 8 (published as the 2003 US National Arboretum "Web Version" of the USDA Plant Hardiness Zone Map USDA Miscellaneous Publication No. 1475, Issued January 1990.

The invention claimed is:

1. A new raspberry plant substantially as illustrated and described herein.

* * * * *